(12) United States Patent
George et al.

(10) Patent No.: US 6,517,853 B1
(45) Date of Patent: Feb. 11, 2003

(54) PROCESS FOR PREPARING A CRYSTAL SUSPENSION

(75) Inventors: Neil George, Huddersfield (GB); Stephen Dawson, Huddersfield (GB); William Malcolm Logan Wood, Huddersfield (GB)

(73) Assignee: Syngenta Limited (GB)

( * ) Notice: Subject to any disclaimer, the term of this patent is extended or adjusted under 35 U.S.C. 154(b) by 63 days.

(21) Appl. No.: 09/715,615

(22) Filed: Nov. 17, 2000

Related U.S. Application Data

(63) Continuation of application No. PCT/GB99/01432, filed on May 7, 1999.

(51) Int. Cl.⁷ ................. A01N 25/04; A01N 47/12; B01F 3/12
(52) U.S. Cl. ................. 424/405; 504/362; 514/937; 516/77; 516/926
(58) Field of Search .............. 516/77, 926; 514/937; 504/362; 424/405

(56) References Cited

U.S. PATENT DOCUMENTS

| | | | |
|---|---|---|---|
| 1,734,975 A | * 11/1929 | Loomis et al. ............ 516/77 X |
| 3,939,260 A | 2/1976 | Lafon |
| 4,330,456 A | 5/1982 | Bonnaud et al. ............... 524/46 |
| 4,880,634 A | 11/1989 | Speiser ........................ 424/450 |
| 5,147,412 A | 9/1992 | Klinksiek et al. ......... 23/293 R |
| 5,471,001 A | 11/1995 | Anderson et al. ............ 562/593 |
| 5,651,991 A | * 7/1997 | Sugiyama et al. ...... 514/937 X |
| 5,871,762 A | * 2/1999 | Venkitaraman et al. . 514/937 X |
| 6,103,267 A | * 8/2000 | Mitchnick et al. ...... 514/937 X |
| 6,207,178 B1 | * 3/2001 | Westesen et al. ........... 424/405 |

FOREIGN PATENT DOCUMENTS

| | | |
|---|---|---|
| EP | 0 221 465 | 10/1986 |
| EP | 0 278 595 A2 | 8/1988 |
| EP | 0 562 391 A1 | 9/1993 |
| GB | 1 569 288 | 6/1980 |
| JP | 01228502 | 9/1989 |
| WO | 92/20420 | 11/1992 |
| WO | 94/20072 | 9/1994 |

* cited by examiner

*Primary Examiner*—Richard D. Lovering
(74) *Attorney, Agent, or Firm*—William A. Teoli, Jr.; Rose M. Allen

(57) ABSTRACT

A process for preparing a crystal suspension of an organic compound which has a $\Delta H/RT$ value (where $\Delta H$ is the heat of fusion of the compound, R is the molar gas constant and T is the melting point of the compound) in the range of 1 to 10, the process comprising dispersing a melt of the organic compound in a liquid dispersion medium, typically water, to form an emulsion, typically an oil-in-water emulsion, cooling the emulsion below the melting point of the organic compound and subjecting the emulsion to ultrasonic vibration.

19 Claims, No Drawings

PROCESS FOR PREPARING A CRYSTAL SUSPENSION

RELATED APPLICATIONS

This application is a continuation of PCT/GB99/01432 filed May 7, 1999, which claims priority to United Kingdom Application No. 9810859.0 filed May 20, 1998.

This invention relates to a crystallisation process and, in particular, to a process for producing a crystalline suspension of an organic compound in a liquid medium.

In many industries, especially in the agrochemical, pharmaceutical and biocide industries, active ingredients are often supplied in the form of suspension concentrates. These comprise a largely insoluble, particulate active ingredient suspended in a liquid medium, usually an aqueous medium. They are commonly prepared by ball or bead milling a millbase consisting of the active ingredient, liquid medium and one or more dispersing agents, and then formulated with additives and a volume-adjusting amount of the liquid medium. Additives may include, for example, antisettling or suspension agents, preservatives, antifoams, antifreezes and biological adjuvants.

It is important to industry to be able to provide fluid, storage stable concentrates without the need for stirred storage vessels or the use of thickeners to maintain the solid particles in suspension. A key factor in obtaining a physically stable product is the particle size of the suspended solid. Normally, the smaller the particle size, the more stable is the suspension.

Milling is a common technique for reducing the particle size of a suspended solid, but may not always produce the best results, and, because it generates considerable heat, may not always be appropriate, for example, where the active ingredient is a low melting solid.

An alternative technique is to crystallise the solid from an emulsion of the melted solid, or a solution of it, in the liquid medium. For example, it is known from E-P-A-0221465 to prepare suspensions by dispersing a melt above its solidification temperature in an aqueous phase and allowing the melt to solidify by cooling it below its crystallisation temperature. It is also known from DE-A-2551841 and DE-A-2900268 that a melt can be dispersed in an aqueous phase having a temperature below the solidification temperature of the melt. Dispersions of this type are produced using high speed stirrers or rotor-stator machines. The disadvantage of these processes is that they tend to give only coarse dispersions with short shelf lives, although finer dispersions may be obtained if, as described in EP-A-0399266, the initial emulsion is subjected to an additional homogenisation step.

In these emulsions, the melt is suspended in the aqueous phase in the form of droplets. If the droplets crystallise rapidly, the crystal size distribution will be the same as the original droplet size within the emulsion. Therefore, in theory, it should be possible to generate finer and more stable dispersions by reducing the droplet size. However, as the droplet size decreases, crystallisation becomes slower. Furthermore, the solubility of the droplet in the continuous phase increases with decreasing droplet size, due to higher pressures within the droplet. The effect of this is that the continuous phase concentration can rise to a level where it becomes supersaturated relative to the crystalline form, with the result that nucleation and crystal growth occurs in the continuous phase. As nucleation rates tend to be slow in the continuous phase, large crystals are generated which bear no resemblance to the original droplets. This is clearly undesirable if fine dispersions are to be obtained.

The use of ultrasound for crystallising melts and solutions is well known. For example, a process for the crystallisation of adipic acid from aqueous solution is known from U.S. Pat. No. 5,471,001. It is also known to use ultrasonics for preparing emulsions and fine droplet dispersions (see, for example, WO-A-94/20072). It has now been found that ultrasound can be used to generate finer particle size, more stable dispersions from emulsions.

Thus, according to the present invention there is provided a process for preparing a crystalline suspension of an organic compound which has a $\Delta H/RT$ value in the range of from 1 to 10, the process comprising dispersing a melt of the organic compound in a liquid dispersion medium to form an emulsion, cooling the emulsion below the melting point of the organic compound and subjecting the emulsion to ultrasonic vibration.

The value $\Delta H/RT$ is a well understood expression which means the enthalpy (heat) of fusion of a compound ($\Delta H$ in kJmol$^{-1}$) at the normal melting point of the compound divided by the molar gas constant (R, where R is 8.31451 Jmol$^{-1}$K$^{-1}$) and the melting point of the compound measured on the absolute or Kelvin scale (in °K). Thus, for example, the $\Delta H/RT$ value of octadecane, which has a melting point of 28.2° C. and a heat of fusion of 61.39 kJmol$^{-1}$ (see the *CRC Handbook of Chemistry and Physics*, [1996–1997], 77$^{th}$ Edition. 6–138) is calculated as follows:

$$61.39/8.31451 \times 10^{-3} \times (28.2+273.16)=24.5$$

The heat of fusion of a compound ($\Delta H$) may be measured by differential scanning calorimetry. A suitable method is described by McNaughton, J. L. and Mortimer, C. T. in IRS: Physical Chemistry Series 2, Butterworth, London 1975, Vol 10; subsequently reprinted by Perkin-Elmer Corpn. Norwalk, Conn., USA.

In a preferred aspect of the invention process, the organic compound has a $\Delta H/RT$ value in the range of from 5 to 10.

The invention is of particular interest in the formulation of low melting agrochemicals, especially pesticides such as fungicides, insecticides and herbicides, and low melting pharmaceutical and biocide products as suspension concentrates. It will be evident, however, that the process is equally applicable to the preparation of a crystalline suspension of any other low melting organic compound.

Where the crystalline suspension is to be stored for long periods at ambient temperature, it is desirable that the organic compound has a mefting point above 20° C. and, preferably, above 30° C. However, the melting point should not be higher than the boiling point of he chosen liquid medium dispersion medium at its operating pressure. This pressure will be as high as it is reasonably practicable or economical to pressurize the apparatus being used. Thus, where the liquid medium is water, as will normally be the case, the organic compound may have a melting point of from 20° C. to 200° C., the upper temperature being possible where the apparatus is pressurized to around 10 bar. Suitably the organic compound will have a melting point of from 20° C. to 120° C. for example, from 30° C. to 100° C. and, typically, from 40° C. to 90° C.

The liquid dispersion medium, which may be any suitable liquid, for example, water or an agriculturally acceptable organic solvent that is benign to living tissue, will ideally have a crystallisation point of at least 10° C., suitably 20° C., below the crystallisation point of the organic compound, and a boiling point of at least the same order as the melting point of the organic compound, and preferably at least 5° C. above the melting point of the organic compound, for example, from 10° C. to 30° C. above. Of most interest, however, are those suspensions where the liquid dispersion medium is an aqueous medium and where the emulsion formed is an oil-in-water emulsion.

Conveniently, the organic compound is melted and heated to a temperature slightly above its melting point, for example 5° C. to 10° C. above, and added to the liquid dispersion medium heated to approximately the same temperature as the melt, ie within 5° C. or so. Alternatively, the organic compound may be added to the liquid medium at a temperature above or below the melting point of the organic compound, for example prior to heating to the melt temperature, and the temperature adjusted until the organic compound has melted.

Depending on the crystallisation properties of the organic compound, it may also be possible to add the melt to the liquid medium at a temperature below the melting point of the organic compound without further heating.

The concentration of the organic compound in the liquid dispersion medium will be up to 60% w/w, normally from 1% w/w to 60% w/w, for example, from 1% w/w to 20% w/w.

The liquid medium may contain additives, for example one or more dispersing agents, or other additives of the type normally used in the preparation of crystalline suspensions and which are well documented in the literature. The amount of additive used will normally be in the range of from 0.01% w/w to 10% w/w, for example from 0.05% w/w to 5% w/w, and typically from 0.1% w/w to 2% w/w of the total dispersion medium.

The liquid medium containing the melt or solution is vigorously agitated using, for example, a high shear mixer or homogeniser or a combination of these, to generate the desired droplet size of the suspended organic compound. Generally, droplet sizes of less than 10 μm (mean diameter), for example between 1 μm and 10 μm and preferably between 1 μm and 5 μm, are required, but the present invention is also applicable to sub-micron droplets.

The emulsion so formed is cooled, preferably as rapidly as possible, to a temperature below the melting point of the organic compound, suitably to a temperature of from 1° C. to 80° C., depending on the melting point of the organic compound and the nature of the liquid dispersion medium. For a compound with a melting point of, for instance, 70° C. to 80° C. and where the liquid dispersion medium is water, the emulsion may be cooled from 30° C. to 70° C., for example from 50° C. to 60° C., below the melting point of the organic compound. For a compound with a melting point of, for instance, 20° C. to 40° C., the emulsion may be cooled from 1° C. to 20° C., for example from 3° C. to 10° C., below the melting point of the organic compound. After cooling, ultrasonic vibration is applied until crystallisation has progressed to an acceptable degree. This may be done either batch-wise or continously by passing a continuous stream of the emulsion through a vessel in which the ultrasonic vibration is applied. Feeding the emulsions through a continuous sonication device may enhance the droplet nucleation rate thereby generating finer, more stable dispersions.

Any suitable source of ultrasonic vibration may be used. A half-inch diameter (12.7 mm) ultrasonic probe operating at 20 kHz and a power input of 100 watts has been found convenient, but there will be many other commercially available devices equally suitable.

The invention is of particular interest for preparing a crystalline suspensions of low melting organic compounds with a suitable ΔH/RT value, such as ibuprofen, piperonal, camphene, 3-iodo-2-propynyl butyl carbamate and like compounds.

The invention is illustrated by the following Examples in which Mowiol[1]18–88, which is a poly(vinyl alcohol) 88% hydrolysed (molecular weight 18,000), is used as a dispersing agent. The following abbreviations are used throughout:

| g = grammes | % w/w = percent weight by weight | ° C. = degrees centigrade |
|---|---|---|
| l = liters | | hr = hour |
| rpm = revolutions per minute | ml = milliliters | ΔH = heat of fusion (kJmol$^{-1}$) |
| | mp = melting point | T = temperature in degrees Kelvin |
| R = molar gas constant (8.31451 Jmol$^{-1}$ k$^{-1}$) | | w = watt |

The name Mowiol is a registered trade mark

EXAMPLE 1

Preparation of an aqueous dispersion (1% w/w) of ibuprofen (α-methyl-4-(2-methylpropyl)benzene acetic acid: mp 74° C., ΔH/RT 9.33).

Ibuprofen (10 g) and an aqueous solution of Mowiol 18–88 (990 g, 2% w/w) in a dispersion vessel were heated to 80° C. using a water bath to melt the ibuprofen. The molten ibuprofen was dispersed in the surfactant solution using a preheated high shear mixer (ultra-turrax, 9500 rpm). The mixture was emulsified for five minutes and produced a stable dispersion with a droplet size of no greater than 10 μm. The hot emulsion was pumped (peristaltic pump, 6 lhr$^{-1}$) through a cooled coil to reduce the emulsion temperature to 20° C., then fed directly into a continuous sonication vessel (approximately 30 ml sonicated volume) fitted with a high intensity sonic probe (500 w). Two samples (50 ml each) were collected. The first was untreated and the second was cooled rapidly using ice/water. The flow rate was then reduced to 2 lhr$^{-1}$ and two samples collected and treated as above.

All four samples showed fine (<10 μm) crystalline needles which formed immediately after sonication. The number of particles in the final dispersion was similar to the number of droplets in the original hot emulsion which indicated nucleation had occurred preferentially in the droplets. There was no effect of flow rate. By contrast, ibuprofen emulsion samples (2% aqueous dispersion) produced in a similar manner, at a fifth of the scale, but which were allowed to cool without sonication, both naturally to room temperature and rapidly using ice/water, contained non-birefringent (i.e. non-crystalline) droplets after 2 hr and then produced large (100–200 μm) twinned crystals when cooled and equilibrated for 18 hrs. The crystals appeared to have grown from a continuous phase.

EXAMPLE 2

Preparation of a more concentrated aqueous dispersion (20% w/w) of ibuprofen than in Example 1.

Ibuprofen (40 g) and an aqueous solution of Mowiol 18–88 (160 g, 2% w/w) in a dispersion vessel were heated to 80° C. using a water bath to melt the ibuprofen. The molten ibuprofen was dispersed in the surfactant solution using a preheated high shear mixer (ultra-turrax, 9500 prm). The mixture was emulsified for five minutes and produced a stable dispersion with a droplet size of no greater than 10 μm. The hot emulsion was pumped (peristaltic pump, 6 lhr$^{-1}$) through a cooled coil to reduce the emulsion temperature to 20° C. then fed directly into a continuous sonication vessel (approximately 30 ml sonicated volume) fitted with a high intensity sonic probe (500 w). Two emulsion samples (50 ml each) were collected. The first was untreated and the second was cooled rapidly in ice/water. The flow rate was then reduced to 2 lhr$^{-1}$ and two samples collected and treated as above. Each emulsion was sampled periodically during cooling by mounting a small sample for image analysis by optical microscope as follows.

A small sample of the cooled sonicated emulsion was transferred using a capillary tube to a microscope slide and was protected with a glass cover slip. The slide was viewed using transmitted light or cross-polarised light (Zeiss microscope) and an image recorded on a calibrated micrograph. The micrograph provides information as to the size ($\mu$m), shape and degree of crystallinity of the droplets or crystals.

All four samples showed fine (<10 $\mu$m) crystalline spheres to have been formed immediately after sonication. The number of spheres/particles in the final dispersion was similar to the number of droplets in the original hot emulsion, which indicated nucleation had occurred preferentially in the droplets.

EXAMPLE 3

Preparation of an aqueous dispersion (1% w/w) of piperonal (3,4-(methylenedioxy)benzaldehyde: mp 35.6° C., $\Delta$H/RT 5.00).

An emulsion of piperonal in surfactant solution was prepared as in Example 1 (substituting piperonal for ibuprofen). The droplet size was estimated to be less than 2 $\mu$m. The hot piperonal emulsion was pumped (peristaltic pump, 6 lhr$^{-1}$) through a cooled coil to reduce the emulsion temperature to 20° C., then fed directly into a continuous sonication vessel (approximately 30 ml sonicated volume) fitted with a high intensity sonic probe (500 w). Two samples were collected. The first was untreated and the second was cooled rapidly in ice/water. The flow rate was then reduced to 2 lhr$^{-1}$ and two samples collected and treated as above.

All four samples produced by sonication showed a mixture of rectangular plates (10–30 $\mu$m) and smaller crystalline material (2–5 $\mu$m). There was no evidence of relay cystallisation (see below).

By way of comparison, piperonal emulsion samples were produced in a similar manner, at a fifth of the scale, but were allowed to cool without sonication, both naturally to room temperature and rapidly using ice/water. Each emulsion was sampled periodically during cooling for image analysis by optical microscope (see Example 2).

The sample allowed to cool naturally produced a multitude of long coiled rods which grew rapidly after nucleation had occurred (2 hr). The length of these crystals was far larger than the dimensions of the droplet, indicating little droplet nucleation and substantial growth from a continuous phase.

The sample cooled rapidly using ice/water produced large (>100 $\mu$m) highly ordered crystalline structures which grew rapidly by a process known as "relay crystallisation". (In relay crystallisation, fewer droplets nucleate and the dispersion is crystallised predominantly by the transmission of crystallinity (from droplet to droplet) in a front moving away from the original event. By contrast, when sonicated, the whole dispersion completely crystallises indicating many more droplet nucleation events.)

EXAMPLE 4

Preparation of a 20% w/w aqueous dispersion of piperonal.

Piperonal (50 g) and an aqueous solution of Mowiol 18–88 (199 g water: 1 g Mowiol) were heated to 50° C. using a water bath to melt the piperonal. The molten piperonal was dispersed in the surfactant solution using a preheated high shear mixer (ultra-turrox, 9500 rpm). The mixture was emulsified for five minutes to produce a stable dispersion with a droplet size of no greater than 10 $\mu$m. Samples of the emulsion were transferred to three small bottles (50 ml) and each was cooled to 28° C. One sample, designated (a), was subjected to ultrasonic vibration using a high intensity sonic probe (500 w) for 30 seconds. Another sample, designated (b), was sonicated for 0.5 seconds at 10 second intervals over a period of 600 seconds. The third sample, designated (c), was not sonicated (untreated).

Each sample was analysed periodically under an optical microscope by the method described in Example 2. The samples which were subjected to either pulsed or constant high energy sonications produced crystalline dispersions where nucleation had clearly occurred within the droplet and some limited growth had continued beyond the droplet boundary producing crystals resembling the size and number of the original droplet dispersion. The untreated sample exhibited rapid relay crystallisation reflecting lower droplet nucleation and high continuous phase growth—the resulting crystals were larger.

EXAMPLE 5

Preparation of an aqueous 1% w/w dispersion of piperonal.

An emulsion of piperonal in surfactant was prepared as in Example 1 (substituting piperonal for ibuprofen) except in this case only 0.1% Mowiol 18–18 was used (10 g piperonal; 989 g water; 1 g Mowiol). The hot piperonal emulsion was pumped (peristaltic pump) at 2 lhr$^{-1}$ through a cooled coil to reduce the emulsion temperature to 28° C. the fed directly into a continuous sonication vessel (approximately 30 ml sonicated volume) fitted with a high intensity sonic probe (500 watt). The processed emulsion was sampled again and the flow rate increased to 6 lhr$^{-1}$. The emulsion was sampled after a period of equilibration. Each sample was analysed periodically by the method described in Example 2. Both samples produced crystalline dispersions where nucleation had clearly occurred within the droplet and some limited growth had continued beyond the droplet boundary producing crystals resembling the size and number of the original droplet dispersion.

By comparison an untreated, under-cooled sample of emulsion collected in the feed tubes had clearly crystallised by the process of relay crystallisation.

EXAMPLE 6

Preparation of an aqueous dispersion (1% w/w) of (−) camphene ((1S)-2,2-dimethyl-3-methylenebicyclo[2.2.1] heptane: mp 40.5° C., $\Delta$H/RT 1.15).

An emulsion of camphene in surfactant solution was prepared as in Example 1 (substituting camphene for ibuprofen). The hot camphene emulsion was pumped (peristaltic pump) at 6 lhr$^{-1}$ through a cooled coil, to reduce the emulsion temperature to 20° C., then fed directly into a continuous sonication vessel (approximately 30 ml sonicated volume) fitted with a high intensity sonic probe (500 w). Two samples were collected. The first was untreated and the second was cooled rapidly in ice/water. The flow rate was then reduced to 2 lhr$^{-1}$ and two samples collected and treated as above.

All four samples showed nucleation to have occured in the majority of the droplets. In the case of the lower flow rate samples the number of spheres/particles in the final dispersion was similar to the number of droplets in the original hot emulsion which indicated nucleation had occurred prefentially in the droplets.

For the higher flow cases there were some plates (30 μm) but mainly small needles (2 μm).

By contrast camphene emulsion samples produced in a similar manner, but which were allowed to cool without sonication, both naturally to room temperature and rapidly using ice/water, showed non-birefringement shapes similar in size to the original dispersion. The edges of the shapes were smooth not faceted.

EXAMPLE 7

Preparation of an aqueous 1% w/w dispersion of camphene.

An emulsion of camphene in surfactant was prepared as in Example 1 (substituting camphene for ibuprofen) except in this case only 0.1% Mowiol 18–88 was used (10 g camphene; 989 g water; 1 g Mowiol).

The hot emulsion was pumped (peristaltic pump) at 2 lhr$^{-1}$ through a cooled coil to reduce the emulsion temperature to 20° C. then fed directly into a continuous sonication vessel (approximately 30 ml sonicated volume) fitted with a high intensity sonic probe (500 watt). The processed emulsion was sampled and the flow rate increased to 6 lhr$^{-1}$. The emulsion was again sampled after a period of equilibration. Each sample was analysed by the method described in Example 2. The sample taken at the higher flow rate produced amorphous droplets, while the sample taken at the lower flow rate showed crystallisation to have occurred within the droplets. An unsonicated sample of the emulsion remained in the amorphorus state.

EXAMPLE 8

Preparation of an aqueous dispersion (1% w/w) of 3-iodo-2-propynyl butyl carbamate (IPBC: mp 67.5° C., ΔH/RT 9.25).

3-Iodo-2-propynyl butyl carbamate (IPBC: 10 g) and an aqueous solution of Mowiol 18–88 (970 g water: 20 g Mowiol) were heated to 80° C. using a water bath to melt the IPBC. The molten IPBC was dispersed in the surfactant solution using a preheated high shear mixer (ultra-turrex, 9500 rpm). The mixture was emulsified for five minutes to produce a stable dispersion with a droplet size of no greater than 10 μm. The hot emulsion was pumped (peristaltic, 6 lhr$^{-1}$) through a cooled coil to reduce the emulsion temperature to 20° C. then fed directly into a continuous sonication vessel (approximately 30 ml sonicated volume) fitted with a high intensity sonic probe (500 watt). Two samples were collected, the first was untreated and the second was cooled rapidly in ice/water. The flow rate was reduced to 2 lhr$^{-1}$ and two samples were treated as above.

When analysed under an optical microscope as described in Example 2, all four sonicated samples showed that fine (<10 μm) crystalline spheres had been formed immediately after sonication. The number of spheres/particles in the final dispersion was similar to the number of droplets in the original hot emulsion which indicated nucleation had occurred preferentially in the droplets. The samples showed no sign of "Ostwäld" ripening (crystal growth) after one week. The change of flow rate resulted in no apparent effect.

For comparative purposes a 1% w/w emulsion of IPBC was prepared in the same way but the hot emulsion was cooled in two batches; the first batch being allowed to cool naturally to room temperature and the second batch being cooled rapidly using a ice/water bath. Each emulsion was sampled periodically during cooling for image analysis as described in Example 2. Both samples produced "fern like" growth with large numbers of small particles growing in clusters (after 30 minutes cooling). On standing for several days the samples had appeared to have ripened and produced larger (25×10 μm) crystals.

What is claimed is:

1. A process for preparing a crystal suspension of an organic compound which has a ΔH/RT value in the range of 1 to 10, the process comprising
   dispersing a melt of the organic compound in a liquid dispersion medium to form an emulsion,
   cooling the emulsion below the melting point of the organic compound, and
   crystallizing the organic compound from the emulsion by ultrasonic vibration to make the crystal suspension of the organic compound.

2. A process according to claim 1 in which the organic compound has a ΔH/RT value in the range of 5 to 10.

3. A process according to claim 1 in which the organic compound has a melting point above 20° C.

4. A process according to claim 1 in which the organic compound has a melting point between 30° C. and 100° C.

5. A process according to claim 1 in which the organic compound is ibuprofen, camphene, piperonal or 3-iodo-2-propynyl butyl carbamate.

6. A process according to claim 1 in which the liquid dispersion medium has a crystallisation point of at least 10° C. below the melting point of the organic compound and a boiling point of at least the same order as the melting point of the organic compound.

7. A process according to claim 1 in which the liquid dispersion medium is an aqueous medium.

8. A process according to claim 1 in which the emulsion formed is an oil-in-water emulsion.

9. A process according to claim 1 in which the melt is added to the liquid dispersion medium while the liquid dispersion medium is at approximately the same temperature as the melt.

10. A process according to claim 1 in which the melt of the organic compound is dispersed in the liquid dispersion medium using a high shear mixer.

11. A process according to claim 1 in which the melt of the organic compound is dispersed in the liquid dispersion medium using a homogeniser.

12. A process according to claim 1 in which the organic compound is dispersed in the liquid dispersion medium in the form of droplets having a mean diameter of from between 1 μm to 10 μm.

13. A process according to claim 1 in which the emulsion is rapidly cooled to a temperature of from 10° C. to 80° C. below the melting point of the organic compound.

14. A process according to claim 1 in which the emulsion is subjected to ultrasonic vibration by passing a continuous stream of the emulsion through a vessel in which the ultrasonic vibration is applied.

15. The process according to claim 1, wherein the organic compound is an agrochemical, a pharmaceutical or a biocide.

16. The process according to claim 1, wherein the organic compound is a pesticide.

17. The process according to claim 1, wherein the organic compound is a fungicide, an insecticide or an herbicide.

18. The process according to claim 1, wherein the concentration of the organic compound in the liquid dispersion medium is from 1% w/w to 60% w/w.

19. The process of claim 1, wherein the liquid dispersion medium comprises one or more additives in an amount of 0.01% w/w to 10% w/w.

* * * * *